United States Patent [19]
Tokumochi et al.

[11] Patent Number: 5,886,045
[45] Date of Patent: Mar. 23, 1999

[54] REMEDY FOR ALLERGIC DISEASES IN THE REGION OF THE NOSE

[75] Inventors: Fuminori Tokumochi, Kobe; Masako Kimura, Kakogawa; Kunihiro Fukushi, Osaka, all of Japan

[73] Assignees: Taiyo Pharmaceutical Co., Ltd., Tokyo, Japan; Senju Pharmaceutical Co., Ltd., Osaka, Japan

[21] Appl. No.: 750,060
[22] PCT Filed: Apr. 22, 1996
[86] PCT No.: PCT/JP96/01083
  § 371 Date: Dec. 4, 1996
  § 102(e) Date: Dec. 4, 1996
[87] PCT Pub. No.: WO96/33741
  PCT Pub. Date: Oct. 31, 1996

[30] Foreign Application Priority Data

Apr. 24, 1995 [JP] Japan ................................ 7-098385

[51] Int. Cl.⁶ ...................................................... A61K 31/16
[52] U.S. Cl. ............................................ 514/599; 514/912
[58] Field of Search ...................................... 514/599, 912

[56] References Cited

U.S. PATENT DOCUMENTS 4,556,737  3/1985  Koda et al. ............................ 514/599

FOREIGN PATENT DOCUMENTS 0 624 367  11/1994  European Pat. Off. .
7-25758  1/1995  Japan .
7-118168  5/1995  Japan .

OTHER PUBLICATIONS

Chemical Abstract an 1992 : 604788, Togawa et al, 1992.

*Primary Examiner*—Keith D. MacMillan
*Attorney, Agent, or Firm*—Wenderoth, Lind & Ponack, L.L.P

[57] ABSTRACT

An anti-allergic pharmaceutical composition for nasal topical administration comprising an IgE antibody production inhibitor as an active ingredient, which is effective and safe in its nasal topical administration.

5 Claims, 1 Drawing Sheet

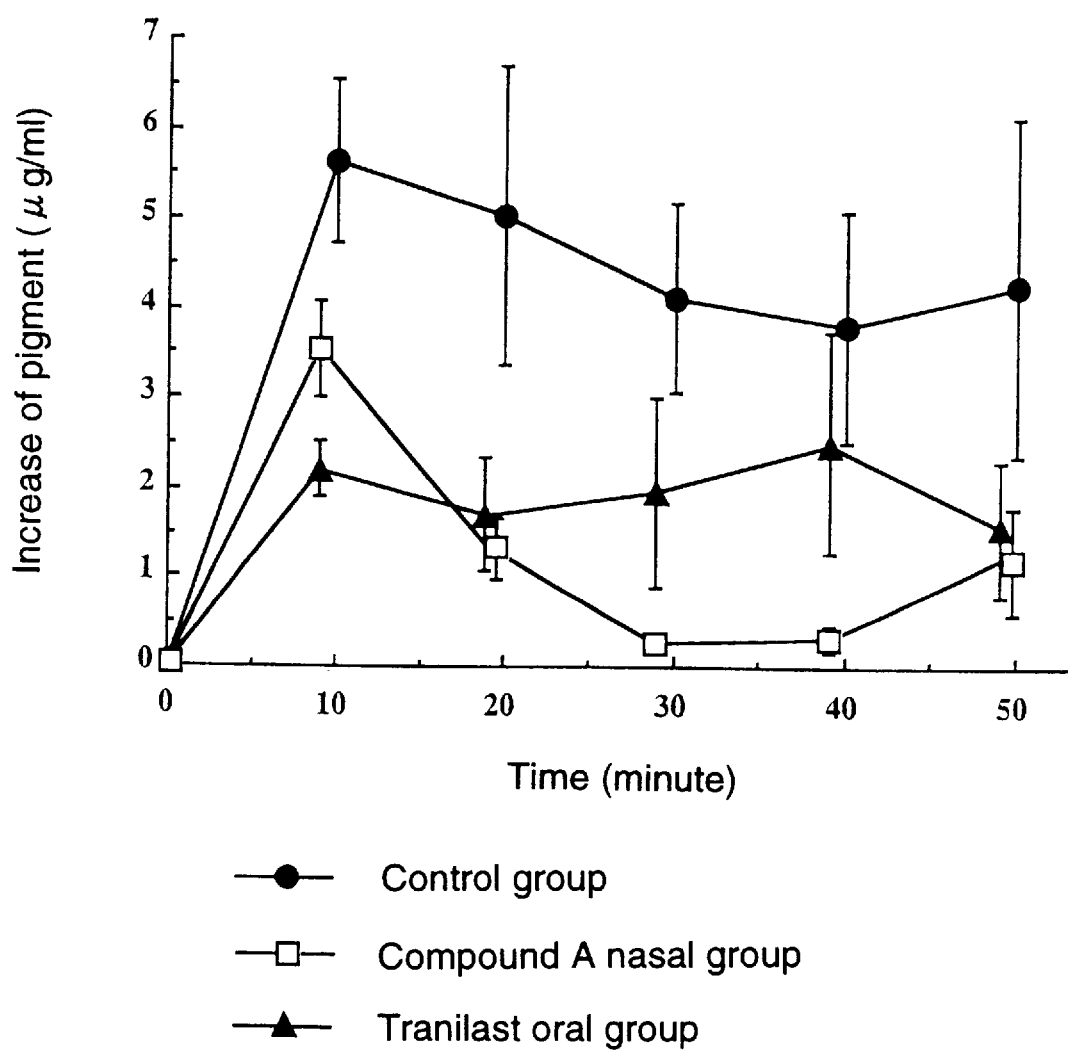

REMEDY FOR ALLERGIC DISEASES IN THE REGION OF THE NOSE

This application is a 371 of PCT/JP96/01083 filed Apr. 22, 1996

FIELD OF THE INVENTION

The present invention relates to an anti-allergic pharmaceutical composition for nasal topical use. Specifically, the present invention relates to an anti-allergic pharmaceutical composition for nasal topical use comprising an IgE antibody production inhibitor as an active ingredient.

BACKGROUND OF THE INVENTION

Allergic reactions include four types of reactions, i.e., types I, II, III and IV. The type I (immediate-type, anaphylactic) allergic reaction is triggered by the reaction-relating-factor immunoglobulin E (hereinafter abbreviated as an IgE antibody). The reaction steps can be divided roughly into the following three steps. The first step is a sensitization step involving IgE antibody production and binding of the resulting IgE antibodies to mast cells or basophils. The second step involves degranulation of the mast cells or basophils and release of chemical mediators. The third steps involves onset of effects of the released chemical mediators on the target organs. Thus, the type I allergic reaction against foreign antigens leads to onset of symptoms through the above reaction steps.

Only symptomatic treatments by inhibiting the above second and/or third reaction steps have been carried out to treat allergic diseases. That is, the treatments are carried out by inhibiting the release of chemical mediators accompanying the degranulation and/or by inhibiting allergic reactions induced by the released chemical mediators. These symptomatic treatments have been known to be effective not only in systemic administration of anti-allergic agents but also in their topical administration to the nose, etc. However, the effects of the treatments are limited because the treatments do not inhibit IgE antibody production which is the basic first step of the type I allergic reaction.

As fundamental remedies against the type I allergic reaction, medicaments inhibiting the above first step, namely IgE antibody production inhibitors, are being developed. Examples of such inhibitors include {2-[4-(3-ethoxy-2-hydroxypropoxy)phenylcarbamoyl]ethyl}dimethylsulfonium p-toluenesulfonate (suplatast tosilate, hereinafter sometimes referred to as Compound A), and ethyl 2,6-bis-(N-methylcarbamoyl)-pyridine-4-carboxylate (hereinafter sometimes referred to as CS-1433). Anti-allergic effects in their systemic administration, namely oral administration, etc., have been reported (JP-A 59-167564, New Current, Vol. 3, No. 26 (1992) etc. for Compound A; Japanese Journal of Allergology, Vol. 36, No. 8 (1987) etc. for CS-1433). Regarding ophthalmic topical administration of Compound A, etc., anti-allergic effects of eye-dropping, etc., of Compound A are reported (EP-A-624, 367, etc.).

However, because the mechanisms of nasal topical IgE antibody production are not clear, there is no report on effects of nasally topically administered drugs applicable to nasal topical membrane allergic reaction.

As described above, there is no satisfactory anti-allergic pharmaceutical compositions that are effective and safe in nasal topical administration. The object of the present invention is to provide an excellent anti-allergic pharmaceutical composition for nasal topical use.

BRIEF DESCRIPTION OF THE DRAWINGS

FIG. 1 is a graph showing the anti-allergic effect of the anti-allergic pharmaceutical composition administered to rats with experimental allergic rhinitis in Test Example 1.

The ordinate indicates the increase ($\mu$g/ml) in the pigment amount from the initial value. The abscissa indicates the time (minute).

DISCLOSURE OF THE INVENTION

The present inventors have intensively studied to obtain an anti-allergic pharmaceutical composition effective and safe in nasal topical administration based on the view that drugs are, in general, preferably administered topically considering the side effect, etc., and that topical administration is preferable to systemic administration considering the delivery of the drugs. As a result, the present invention has been accomplished.

That is, the present invention provides an effective and safe anti-allergic pharmaceutical composition for nasal topical use comprising an IgE antibody production inhibitor as an active ingredient.

The present invention also provides a method of treating a nasal topical allergic disease, which comprises administering intramucosally an effective amount of an IgE antibody production inhibitor for treating a nasal topical allergic disease.

The present invention also provides use of an IgE antibody production inhibitor for the manufacture of an anti-allergic pharmaceutical composition for nasal topical use.

Specifically, the present invention provides an effective and safe anti-allergic pharmaceutical composition for nasal topical administration comprising as an active ingredient{2-[4-(3-ethoxy-2-hydroxypropoxy)phenylcarbamoyl]-ethyl}dimethylsulfonium p-toluensulfonate (i.e., Compound A) of the formula (I):

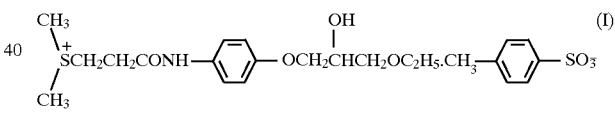

Examples of the IgE antibody production inhibitors as an active ingredients of the pharmaceutical composition of the present invention include Compound A described above, CS-1433, etc. The physical and chemical properties and the production of Compound A are described, for example, in JP-A 59-167564.

As is clear from Experiments hereinafter, although topical nasal intramucosal administration of the pharmaceutical composition of the present invention exhibits excellent IgE antibody production inhibitory effects, the nasal topical administration has no effects on the systemic IgE antibody production. Therefore the pharmaceutical composition of the present invention can be used as an effective and safe drug to treat nasal topical allergic diseases (e.g., allergic rhinitis, etc.).

The pharmaceutical composition of the present invention can be produced, for example, by mixing an IgE antibody production inhibitor (e.g., Compound A, etc.) with per se known pharmacologically acceptable carriers, excipients, diluents, etc., and may be formulated into parenteral compositions such as nasal drops (nasal solutions or suspensions), nasal ointments, etc., by known methods.

When the pharmaceutical composition of the present invention is used as nasal drops, it may contain additives such as buffers, isotonizing agents, preservatives, pH adjustors, thickeners, chelating agents, suspending agents, etc., which are commonly used in nasal drops unless they are unsuited for the purpose of the present invention.

Examples of such buffers include phosphate buffers (e.g., sodium dihydrogenphosphate dihydrate, etc.), carbonate buffers (e.g., sodium bicarbonate, etc.), borate buffers (e.g., borax, etc.), citrate buffers (e.g., trisodium citrate dihydrate, etc.), tartrate buffers (e.g., sodium tartrate, etc.), acetate buffers (e.g., sodium acetate, etc.), and amino acids (e.g., sodium glutamate, $\epsilon$-aminocaproic acid, etc.).

Examples of such isotonizing agents include saccharides such as sorbitol, glucose and mannitol; polyhydric alcohols such as glycerin, polyethylene glycol and propylene glycol; and salts such as sodium chloride.

Examples of such preservatives include benzalkonium chloride, benzethonium chloride, parahydroxybenzoates (e.g., methyl parahydroxybenzoate, ethyl parahydroxybenzoate, etc.), benzyl alcohol, phenethyl alcohol, sorbic acid or salts thereof, thimerosal, and chlorobutanol.

Examples of such pH adjustors include hydrochloric acid, acetic acid, phosphoric acid, sodium hydroxide, potassium hydroxide, and borax.

Examples of such thickeners include hydroxyethylcellulose, hydroxypropylcellulose, methylcellulose, hydroxypropylmethylcellulose, carboxymethylcellulose and salts thereof.

Examples of such chelating agents include disodium edetate, and condensed sodium phosphate.

Examples of such suspending agents include polysorbate 80.

When the anti-allergic pharmaceutical composition of the present invention is used as nasal drops, examples of the solvents include sterile purified water, distilled water for injection, water for injection, and castor oil.

When the pharmaceutical composition of the present invention is used as nasal ointments, examples of the nasal ointment bases include purified lanolin, white soft paraffine, plastibase, and liquid paraffin.

The pharmaceutical composition of the present invention may contain one or more other anti-allergic agents unless they are unsuited for the purpose of the present invention.

Further, the pharmaceutical composition of the present invention may contain, in addition to the above IgE antibody production inhibitor as the active ingredient, other ingredients having other pharmacological activity unless they are unsuited for the purpose of the present invention.

The pharmaceutical composition of the present invention has low toxicity, and can safely be administered parenterally to mammals (e.g., humans, monkeys, cattle, horses, dogs, cats, rabbits, mice, rats, etc.).

The dose of the pharmaceutical composition of the present invention varies with the administration route, symptoms, age and body weight of the patient, etc. For example, when the pharmaceutical composition in the form of nasal drops is administered to a human adult patient with an allergic disease, preferably, one to several drops of the nasal drops containing Compound A as an active ingredient in an amount of about 0.01 to 10.0 w/v %, preferably about 0.1 to 7.5 w/v %, more preferably 0.5 to 5.0 w/v %, is administered 1 to 5 times per day depending upon the symptom. When the pharmaceutical composition in the form of nasal ointments is administered to a human adult patient with an allergic disease, the nasal ointments containing Compound A as an active ingredient in an amount of about 0.01 to 10.0 w/w %, preferably about 0.1 to 7.5 w/w %, more preferably 0.5 to 5.0 w/w %, is preferably administered 1 to 5 times per day depending upon the symptom by applying the ointments spread on a nasal stick to the nasal cavity with gentle massage.

EXAMPLES

The following examples further illustrate the present invention in detail and the following test examples show effects of the present invention, but are not to be construed to limit the scope thereof.

Example 1

Nasal drops (nasal solution)

By a conventional method, a nasal solution having the following formulation was prepared.

| | |
|---|---|
| Compound A | 0.5 g |
| Sodium chloride | 0.9 g |
| Sodium dihydrogenphosphate dihydrate | 0.1 g |
| Benzalkonium chloride | 0.005 g |
| Sodium hydroxide | suitable amount (pH 6.0) |

Sterile purified water was added to a total volume of 100 ml.

Example 2

Nasal drops (nasal solution)

By a conventional method, a nasal solution having the following formulation was prepared.

| | |
|---|---|
| Compound A | 5.0 g |
| Conc. glycerin | 2.6 g |
| Sodium acetate | 0.1 g |
| Benzalkonium chloride | 0.005 g |
| Diluted hydrochloric acid | suitable amount (pH 5.0) |

Sterile purified water was added to a total volume of 100 ml.

Example 3

Nasal drops (nasal solution)

By a conventional method, a nasal solution having the following formulation was prepared.

| | |
|---|---|
| Compound A | 3.0 g |
| Mannitol | 5.0 g |
| Sodium acetate | 0.1 g |
| Chlorobutanol | 0.2 g |
| Benzethonium chloride | 0.005 g |
| Diluted hydrochloric acid | suitable amount (pH 4.0) |

Sterile purified water was added to a total volume of 100 ml.

Example 4

Nasal drops (nasal solution)

By a conventional method, a nasal solution having the following formulation was prepared.

| Compound A | 2.0 g |
| --- | --- |
| Conc. glycerin | 2.6 g |
| Sodium acetate | 0.05 g |
| Hydroxypropylmethylcellulose | 0.1 g |
| Methyl parahydroxybenzoate | 0.02 g |
| Propyl parahydroxybenzoate | 0.01 g |
| Diluted hydrochloric acid | suitable amount (pH 5.5) |

Sterile purified water was added to a total volume of 100 ml.

Example 5
Nasal drops (nasal solution)

By a conventional method, a nasal solution having the following formulation was prepared.

| Compound A | 1.0 g |
| --- | --- |
| Sodium chloride | 0.9 g |
| Trisodium citrate dihydrate | 0.02 g |
| Methyl parahydroxybenzoate | 0.02 g |
| Chlorobutanol | 0.1 g |
| Acetic acid | suitable amount (pH 4.5) |

Sterile purified water was added to a total volume of 100 ml.

Example 6
Nasal ointment

By a conventional method, a nasal ointment having the following formulation was prepared.

| Compound A | 1.0 g |
| --- | --- |
| Liquid paraffin | 1.0 g |

White soft paraffine was added to a total amount of 100 g.

Example 7
Nasal drops (nasal solution)

By a conventional method, a nasal solution having the following formulation was prepared.

| Compound A | 2.0 g |
| --- | --- |
| Conc. glycerin | 2.6 g |
| Sodium dihydrogenphosphate | 0.1 g |
| Benzalkonium chloride | 0.005 g |
| Sodium hydroxide | suitable amount (pH 6.0) |

Sterile purified water was added to a total volume of 100 ml.

Example 8
Nasal drops (nasal solution)

By a conventional method, a nasal solution having the following formulation was prepared.

| Compound A | 0.2 g |
| --- | --- |
| Sodium chloride | 0.9 g |
| Sodium acetate | 0.1 g |

-continued

| Benzalkonium chloride | 0.005 g |
| --- | --- |
| Acetic acid | suitable amount (pH 4.5) |

Sterile purified water was added to a total volume of 100 ml.

Example 9
Nasal drops (nasal solution)

By a conventional method, a nasal solution having the following formulation was prepared.

| Compound A | 5.0 g |
| --- | --- |
| Sodium chloride | 0.9 g |
| Sodium acetate | 0.05 g |
| Methyl parahydroxybenzoate | 0.026 g |
| Propyl parahydroxybenzoate | 0.014 g |
| Chlorobutanol | 0.3 g |
| Diluted hydrochloric acid | suitable amount (pH 4.5) |

Test Example 1

The effects of the pharmaceutical composition of the present invention administered to actively sensitized rats with experimental allergic rhinitis were examined using as an index the pigment leakage in the nasal membrane.

Test Animals:

Sprague-Dawley male rats weighing about 250 g were used. The rats were reared in a rearing room at a temperature of 23±2° C. and a humidity of 55±10% by freely giving feed (Labo MR Stock, manufactured by Nippon Nosan Kogyo Kabushiki Kaisha) and water to them.

Test Compounds:

The 5% Compound A nasal solution (hereinafter referred to as the Compound A nasal solution) of Example 9 was used as a representative example of the pharmaceutical composition of the present invention. A solution of tranilast (100 mg/kg rat) in an aqueous solution of the same molar amount of sodium bicarbonate (hereinafter referred to as the tranilast oral solution) was used as a reference substance. Physiological saline was used as a control.

Grouping of the Test Animals:

Eight rats were used in each of the Compound A nasal solution—administered group (hereinafter referred to as the Compound A nasal group), the tranilast oral solution—orally administered group (hereinafter referred to as the tranilast oral group), and the physiological saline nasal drops—administered group (hereinafter referred to as the control group).

Test Methods and Test Results:

A solution of ovalbumin (hereinafter abbreviated as OA) (1 mg) in physiological saline (1 ml) was administered intramuscularly to the femoral muscle of the rats in divided portions. At the same time, killed Bordetella pertussis ($2 \times 10^{10}$ cells) were administered intraperitoneally as an adjuvant to obtain actively sensitized animals. The rats were anesthetized with pentobarbital 12 to 14 days after the sensitization. After a cannula was inserted for securing airway passage, the esophagus was ligated. A polyethylene tube was inserted from the esophagus to the postnares, and physiological saline was perfused at a flow rate to 0.25 ml/minute with a perfusion pump.

Then, 4% brilliant blue (0.5 μl/kg) was administered intravenously, and the perfusion solution effused from the nasal rostrum was collected for 10 minutes. The amount of the pigment in each solution was measured and considered to be an initial value. A solution of OA (3 mg/ml) in physiological saline was perfused, and the perfusion solution was collected 5 times every 10 minutes in the same manner. The amount of the pigment in the perfusion solution was measured, and the increase of the pigment amount from the initial value was determined. The results are shown in FIG. 1.

The Compound A nasal solution and the physiological saline (each 20 μl) were dropped to both nasal cavities 4 times per day for consecutive 20 days beginning 5 days before the sensitization. The tranilast oral solution (1 ml) was orally administered once per day. Statistical analysis was performed with Dunnett's test.

As shown in FIG. 1, the pigment leakage was significantly (p<0.05) inhibited in both the Compound A nasal group and the tranilast oral group compared to the control group, and the topical nasal administration exhibited excellent anti-allergic effects. In particular, it was found that the Compound A nasal group exhibited the anti-allergic effects more rapidly than the tranilast oral group after the administration.

Test Example 2

The effects of the pharmaceutical composition of the present invention on systemic IgE antibody production were examined using rats.

Test Animals:

Sprague-Dawley male rats weighing about 250 g were used. The rats were reared in a rearing room at a temperature of 23±2° C. and a humidity of 55±10% by freely giving feed (Labo MR Stock, manufactured by Nippon Nosan Kogyo Kabushiki Kaisha) and water to them.

Test Compounds:

The Compound A nasal solution used in Test Example 1 was used as a Compound A—containing nasal solution. A solution of Compound A (10 mg/kg rat) in distilled water was used as a Compound—containing oral solution. Physiological saline was used as a control.

Grouping of the Test Animals:

The rats were divided into the following 3 groups: the Compound A nasal solution—administered group (hereinafter referred to as the Compound A nasal group), the Compound A oral solution—orally administered group (hereinafter referred to as the Compound A oral group), and the physiological saline nasal drops—administered group (hereinafter referred to as the control group). Each group consisted of 7 rats.

Test Methods and Test Results:

A solution of OA (1 mg) in physiological saline (1 ml) was administered intramuscularly to the femoral muscle of the rats in divided portions. At the same time, killed Bordetella pertussis ($2\times10^{10}$ cells) were administered intraperitoneally as an adjuvant to obtain actively sensitized animals. Blood was drawn 12 to 14 days after the sensitization. The anti-OA IgE antibody valence was determined according to the method of Ovary Z., (Progress of Allergy, Vol. 5, p. 459(1958)) to quantify the serum IgE antibody, and the effects of each test compound on the serum IgE antibody level were examined. The results are shown in Table 1.

The Compound A nasal solution and the physiological saline (each 20 μl) was dropped to both nasal cavities 4 times per day for 20 consecutive days beginning 5 days before the sensitization. The Compound A oral solution (1 ml) was orally administered once per day. Statistical analysis was performed with Wilcoxon rank sum test.

TABLE 1

| Effects of each test compound on the serum IgE antibody level | |
|---|---|
| Group | PCA titer (Log$_2$) |
| Compound A oral group | 7.56 ± 0.34 * |
| Compound A nasal group | 9.71 ± 0.42 |
| Control group | 9.75 ± 0.73 |

Note: In the above table, each value is represented as means ± standard errors. The symbol * means that there is a significant difference. * : P < 0.05

Test Results:

As shown in Table 1, the Compound A oral group showed a significant difference (1:$2^{7.56\pm0.34}$ (about 188.7-fold)) (p<0.05) in the PCA titer, showing systemic IgE antibody production inhibitory effects. By contrast, the value of the Compound A nasal group (1:$2^{9.71\pm0.24}$ (837.5-fold)) was as high as that of the control group, and thus it was found that systemic IgE antibody production is not affected.

The results in Test Examples 1 and 2 described above show that nasal topical administration of Compound A has no effect on the systemic IgE antibody production, although the nasal topical administration exhibits excellent IgE antibody production inhibitory effects.

As described above, nasal topical administration of the pharmaceutical composition of the present invention has no effects on the systemic IgE antibody production, although the nasal topical administration exhibits excellent IgE antibody production inhibitory effects. Therefore the pharmaceutical composition of the present invention can safely be used to treat nasal topical allergic diseases.

We claim:

1. A method of treating a nasal allergic disease in a mammal which comprises administering intramucosally to the nose of the mammal in need of such treatment, an effective amount of an IgE antibody production inhibitor compound of the formula (I):

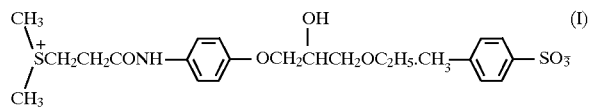

or a pharmaceutically acceptable salt thereof.

2. The method according to claim 1, wherein the compound of the formula (I) is formulated into nasal drops.

3. The method according to claim 2, wherein the compound of the formula (I) is formulated in an amount of 0.01 to 10.0 w/v %.

4. The method according to claim 1, wherein the compound of the formula (I) is formulated into a nasal ointment.

5. The method according to claim 4, wherein the compound of the formula (I) is formulated in an amount of 0.01 to 10.0 w/w %.

* * * * *